United States Patent [19]

Klemarczyk et al.

[11] 4,431,577

[45] * Feb. 14, 1984

[54] CARBOMETHOXY METHYL NORBORNANES, ORGANOLEPTIC USES THEREOF AND PROCESS FOR PREPARING SAME

[75] Inventors: Philip T. Klemarczyk, Old Bridge; James M. Sanders, Eatontown; Manfred H. Vock, Locust; Joaquin F. Vinals, Red Bank; Frederick L. Schmitt, Holmdel; Edward J. Granda, Englishtown, all of N.J.

[73] Assignee: International Flavors & Fragrances Inc., New York, N.Y.

[ * ] Notice: The portion of the term of this patent subsequent to Feb. 15, 2000 has been disclaimed.

[21] Appl. No.: 380,424

[22] Filed: May 20, 1982

Related U.S. Application Data

[62] Division of Ser. No. 284,107, Jul. 16, 1981, Pat. No. 4,350,823, which was a continuation-in-part of Ser. No. 133,870, Mar. 25, 1980, now U.S. Pat. No. 4,319,036.

[51] Int. Cl.³ .......................... A61K 7/46; C11B 9/00
[52] U.S. Cl. ............................................... 252/522 R
[58] Field of Search .................................... 252/522 R

[56] References Cited

U.S. PATENT DOCUMENTS 4,374,054 2/1983 Klemarczyk et al. .......... 252/522 R

Primary Examiner—Helen M. S. Sneed
Attorney, Agent, or Firm—Arthur L. Liberman

[57] ABSTRACT

Described are compounds defined according to the generic structure:

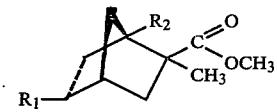

wherein the dashed line represents a carbon-carbon single bond or a carbon-carbon double bond; and one of $R_1$ and $R_2$ is methyl and the other of $R_1$ and $R_2$ is hydrogen. In addition, organoleptic uses of such compounds are disclosed for augmenting or enhancing the aroma or taste of consumable materials including foodstuffs, chewing gums, chewing tobaccos, medicinal products, toothpastes, perfumes, perfumed articles (such as liquid or solid, anionic, cationic, nonionic or zwitterionic detergents), fabric softeners and dryer-added fabric softener articles.

4 Claims, 4 Drawing Figures

FIG. 3 NMR SPECTRUM FOR FRACTION 3 OF EXAMPLE II.

CARBOMETHOXY METHYL NORBORNANES, ORGANOLEPTIC USES THEREOF AND PROCESS FOR PREPARING SAME

This is a divisional of application Ser. No. 284,107, filed July 16, 1981, now U.S. Pat. No. 4,350,823 issued on Sept. 21, 1982 which, in turn, is a continuation-in-part of application for U.S. Letters Patent Ser. No. 133,870 filed on Mar. 25, 1980, now U.S. Pat. No. 4,319,036 issued on Mar. 9, 1982.

BACKGROUND OF THE INVENTION

The present invention relates to carbomethoxy methyl norbornanes having the generic formula:

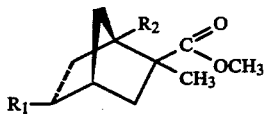

wherein the dashed line represents a carbon-carbon single bond or a carbon-carbon double bond; and one of $R_1$ and $R_2$ is methyl and the other of $R_1$ and $R_2$ is hydrogen, and to novel compositions using one or more of such norbornane derivatives to alter, modify or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Application for U.S. Letters Patent, Ser. No. 133,870 filed on Mar. 25, 1980 relates to compounds generic to the compounds of the instant invention; carboalkoxy alkyl norbornanes having the generic formula:

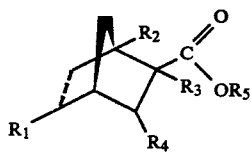

wherein the dashed line represents either a carbon-carbon single or a carbon-carbon double bond; $R_1$, $R_2$, $R_3$ and $R_4$ represent hydrogen or methyl; with the proviso that one of $R_1$ or $R_2$ is methyl and the other of $R_1$ or $R_2$ is hydrogen; and with the further proviso that $R_3$ and $R_4$ are not both methyl, produced by the novel process of our invention and to novel compositions using one or more of such norbornane derivatives to alter, modify or enhance the flavor and/or aroma of consumable materials or impart flavor and/or aroma to consumable materials.

Mellor and Webb, J. Chem. Soc. Perkin Trans II, 1974 (I) 26–31 discloses production of the compounds having the structures:

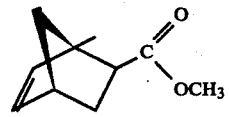

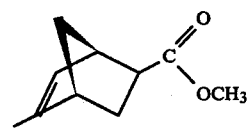

together with several other methyl substituted isomers thereof in admixture, according to the reaction:

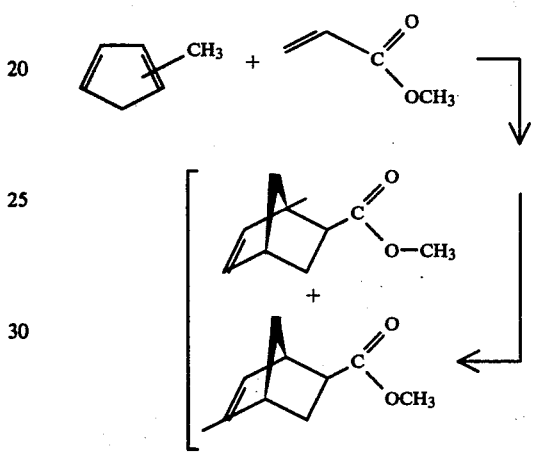

The Mellor and Webb article, however, does not disclose the reaction to take place at low temperatures in the presence of an alkyl aluminum halide or dialkyl aluminum halide whereby but two isomers are produced in a controlled fashion in high yields thus yielding an organoleptically acceptable mixture of carboalkoxy norbornane derivatives.

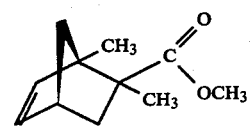

and

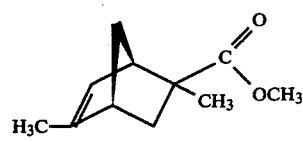

Figure 2:
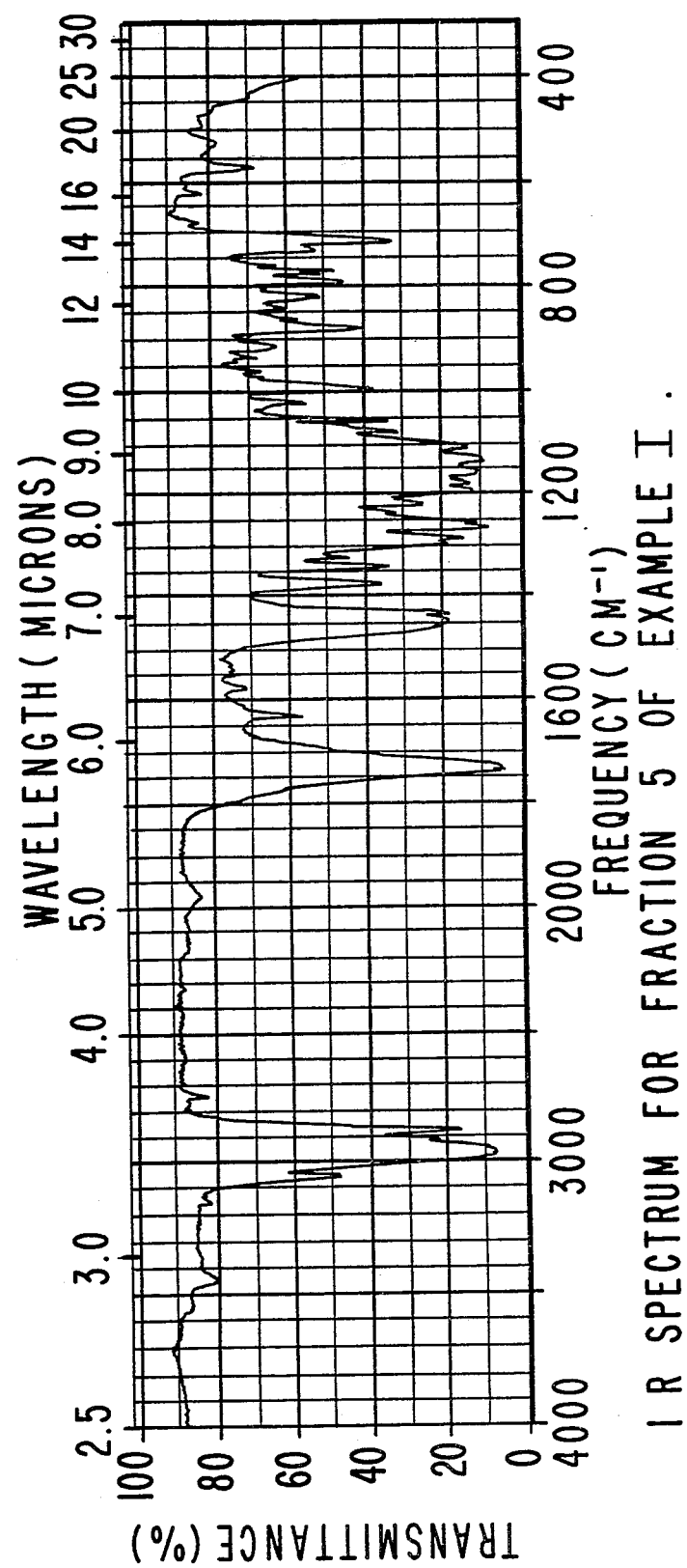

FIG. 2 is the infra-red spectrum for fraction 5 of the distillation product of the reaction product of Example I containing the compounds having the structures:

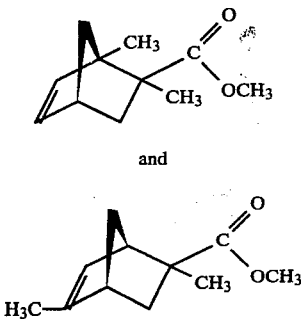

and

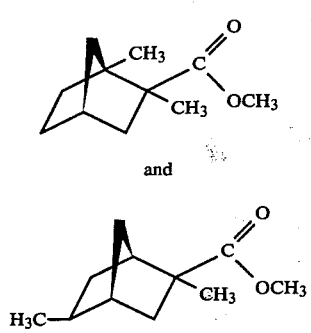

Figure 3:
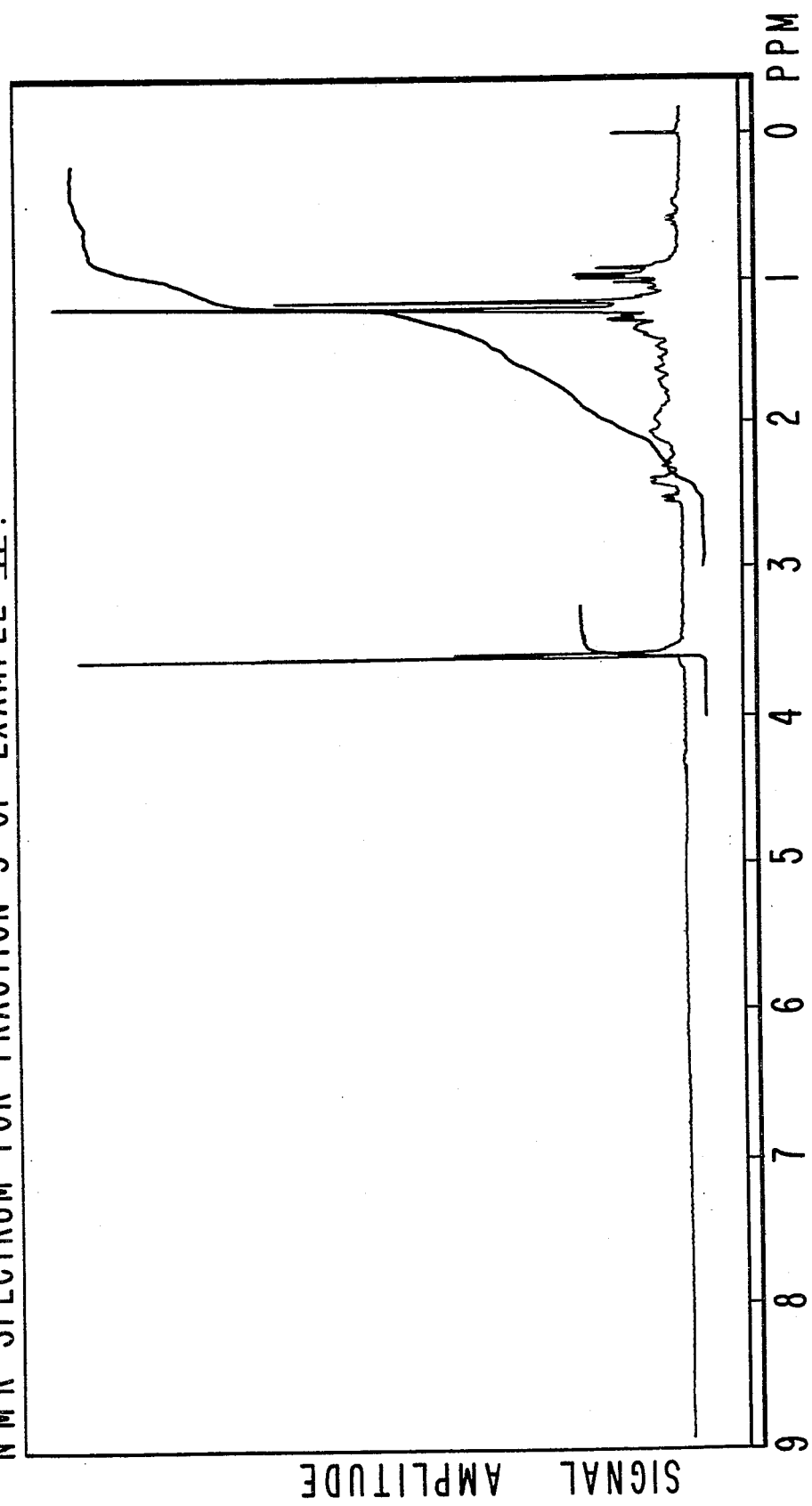

FIG. 3 is the NMR spectrum for fraction 3 of the distillation product of the reaction product of Example II containing the compounds having the structures:

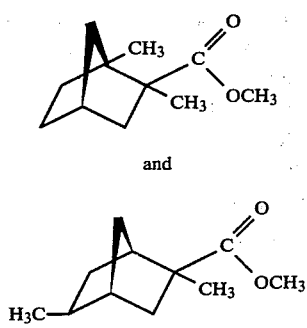

Figure 4:
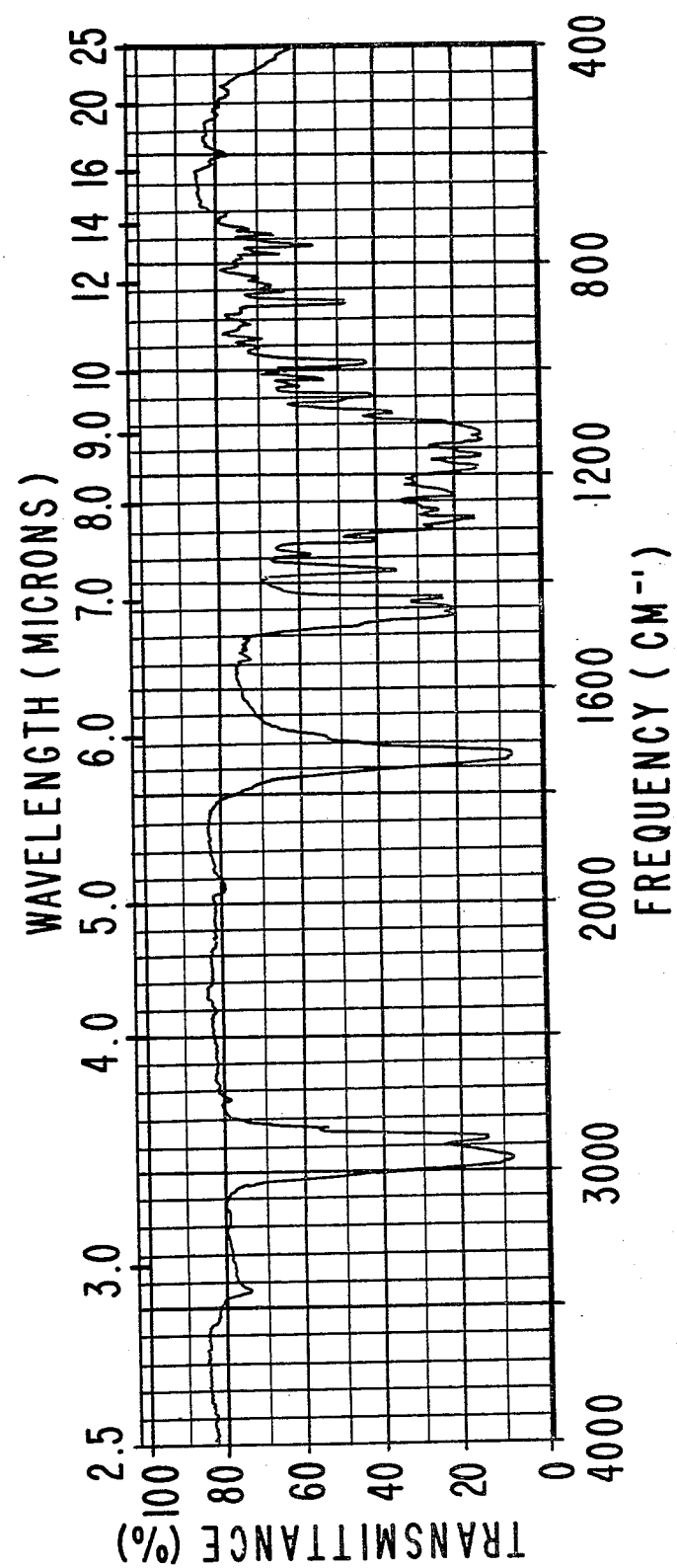

FIG. 4 is the infra-red spectrum for fraction 3 of the distillation product of the reaction product of Example II containing the compounds having the structures:

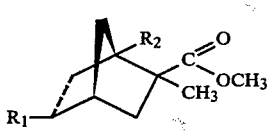

THE INVENTION

The invention provides compounds defined according to the generic structure:

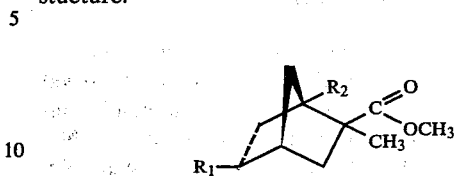

wherein the dashed line represents a carbon-carbon single bond or a carbon-carbon double bond; and one of $R_1$ and $R_2$ is methyl and the other of $R_1$ and $R_2$ is hydrogen. This invention also defines organoleptic uses of such compounds in food flavors, chewing gum flavors, medicinal product flavors, toothpaste flavors, fragrances, colognes and perfumed articles, e.g., solid or liquid anionic, cationic, nonionic or zwitterionic detergents.

The compounds defined according to the generic stucture:

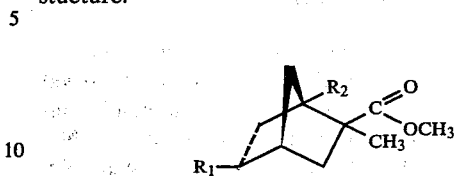

wherein the dashed line represents a carbon-carbon single bond or a carbon-carbon double bond; and one of $R_1$ and $R_2$ is methyl and the other of $R_1$ and $R_2$ is hydrogen, are specifically defined according to the structures:

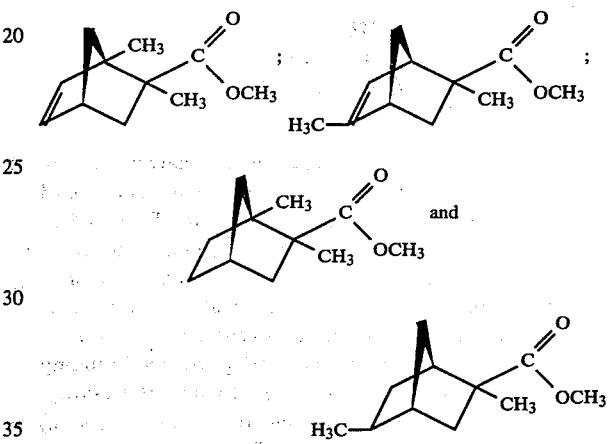

The compounds are specifically produced by reacting methyl methacrylate with methyl cyclopentadiene to produce the compounds having the structures:

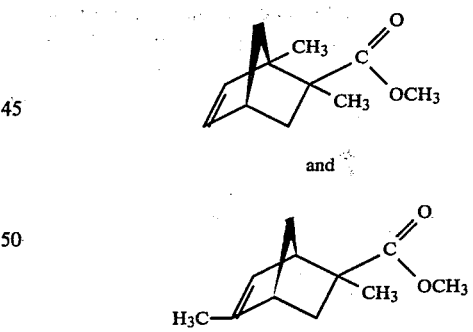

These materials may be used as is and purified as by distillation and preparative chromatography; and/or the materials may be further reacted with a reducing agent such as hydrogen to form additional compounds of our invention defined according to the structures:

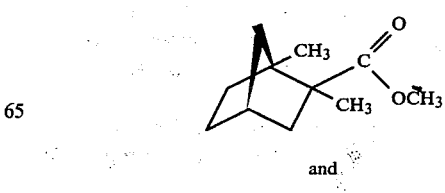

and

-continued

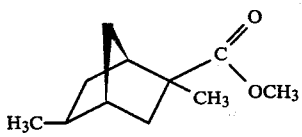

Thus, the reactions to produce the compounds of our invention are as follows:

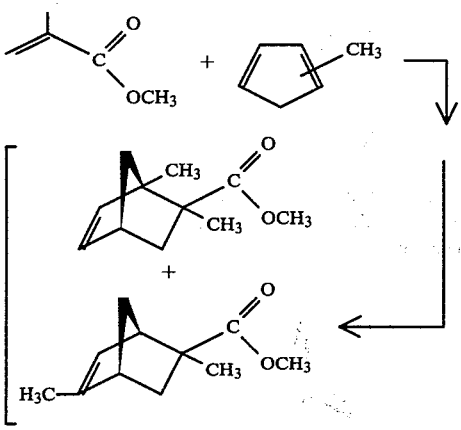

and

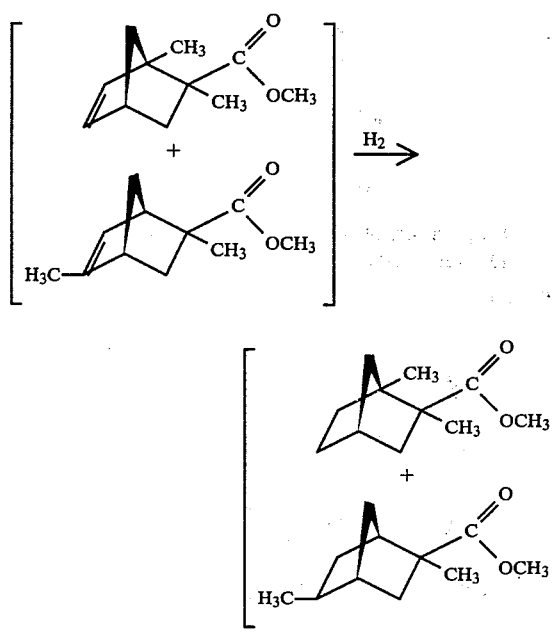

The specific conditions for carrying out the reactions of our invention are set forth in parent application for U.S. Letters Patent, Ser. No. 133,870 filed on Mar. 25, 1980 and co-pending application, Ser. No. 206,466 filed on Nov. 13, 1980. The disclosures of Ser. No. 133,870 filed on Mar. 25, 1980 as well as Ser. No. 206,466 filed on Nov. 13, 1980 are hereby incorporated by reference to the instant disclosure.

The ranges of utility for their organoleptic properties in consumable materials of the substances of our invention are identical to those ranges set forth in Ser. No. 133,870 filed on Mar. 25, 1980 as well as Ser. No. 206,466 filed on Nov. 13, 1980.

The organoleptic properties of the compounds of our invention are as follows:

TABLE I

| Structure of Chemical | Organoleptic Properties in Flavors | Organoleptic Properties in Fragrances |
| --- | --- | --- |
| Mixture of compounds (as produced according to Example I) containing compounds having the structures:<br><br>[structure 1]<br><br>and<br><br>[structure 2] | Blueberry, balsamic and piney aroma and taste. | A powerful, minty, camphoraceous, fruity aroma. |
| Mixture of compounds (produced according to Example II) containing the compounds having the structures:<br><br>[structure 3]<br><br>and<br><br>[structure 4] | A blueberry, patchouli-like, camphoraceous aroma with a blueberry, camphoraceous-like flavor profile at 5 ppm. | A camphoraceous, sweaty, menthol-like aroma with patchouli-like undertones. |

The following examples set forth embodiments of our invention as it is preferred to practice it. The invention is not to be limited thereby but is only limited to the scope of the claims which follow said examples.

EXAMPLE I

Preparation of Methyl Ester of 2,5(and 6)Dimethyl-5-Norbornene-2-Carboxylic Acid Reaction:

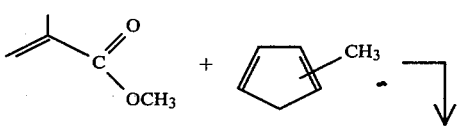

-continued

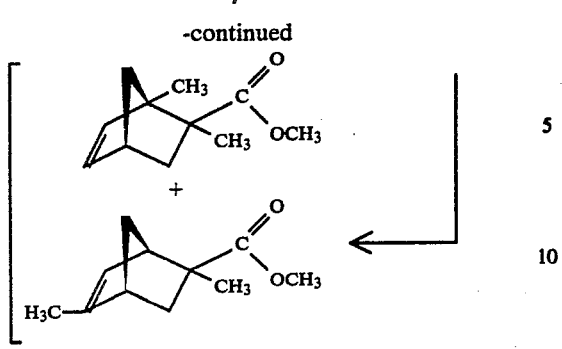

Into a 5,000 cc reaction flask equipped with stirrer, condenser, thermometer and dropping funnel and nitrogen blanket apparatus is placed 0.1 moles of ethyl aluminum dichloride and 1,000 cc anhydrous toluene. 460 grams (4.6 moles) of methyl methacrylate is added drop-wise to the reaction mass over a period of 40 minutes while maintaining the temperature thereof at 25°-30° C. Over a period of 1 hour and 15 minutes while maintaining the reaction temperature at 25°-30° C., 800.0 grams (4.6 moles) of methyl cyclopentadiene (46% in toluene) is added to the reaction mass. After addition of the methyl cyclopentadiene, the reaction mass is stirred at room temperature for a period of 45 minutes whereupon the indications are that the reaction has gone to completion. 300 cc of 10% hydrochloric acid is then added to the reaction mass. The reaction mass now exists in two phases; an organic phase and an aqueous phase. The organic phase is washed with two 500 cc portions of 10% sodium bicarbonate and one 300 cc portion of 10% sodium chloride. The reaction mass is then stripped and distilled yielding the following fractions (12" Stone column):

| Fraction Number | Vapor Temp. (°C.) | Liquid Temp. (°C.) | Pressure mm/Hg. |
|---|---|---|---|
| 1 | 50/55 | 75/75 | 3.5/3.0 |
| 2 | 55 | 80 | 3.0 |
| 3 | 55 | 80 | 3.0 |
| 4 | 55 | 85 | 3.0 |
| 5 | 55 | 85 | 3.0 |
| 6 | 55 | 89 | 3.0 |
| 7 | 55 | 190 | 3.5 |

The reaction mass is then redistilled on an 18" Goodloe packed column yielding the following fractions:

| Fraction Number | Vapor Temp. (°C.) | Liquid Temp. (°C.) | Pressure mm/Hg. |
|---|---|---|---|
| 1 | 60/60 | 70/70 | 3.0/3.0 |
| 2 | 60 | 70 | 3.0 |
| 3 | 60 | 70 | 3.5 |
| 4 | 55 | 68 | 3.0 |
| 5 | 55 | 67 | 2.8 |
| 6 | 54 | 66 | 2.0 |
| 7 | 54 | 65 | 2.5 |
| 8 | 55 | 66 | 2.5 |
| 9 | 55 | 66 | 2.5 |
| 10 | 55 | 66 | 2.5 |
| 11 | 55 | 68 | 2.5 |
| 12 | 54 | 70 | 2.5 |
| 13 | 54 | 88 | 2.0 |

Figure 1:
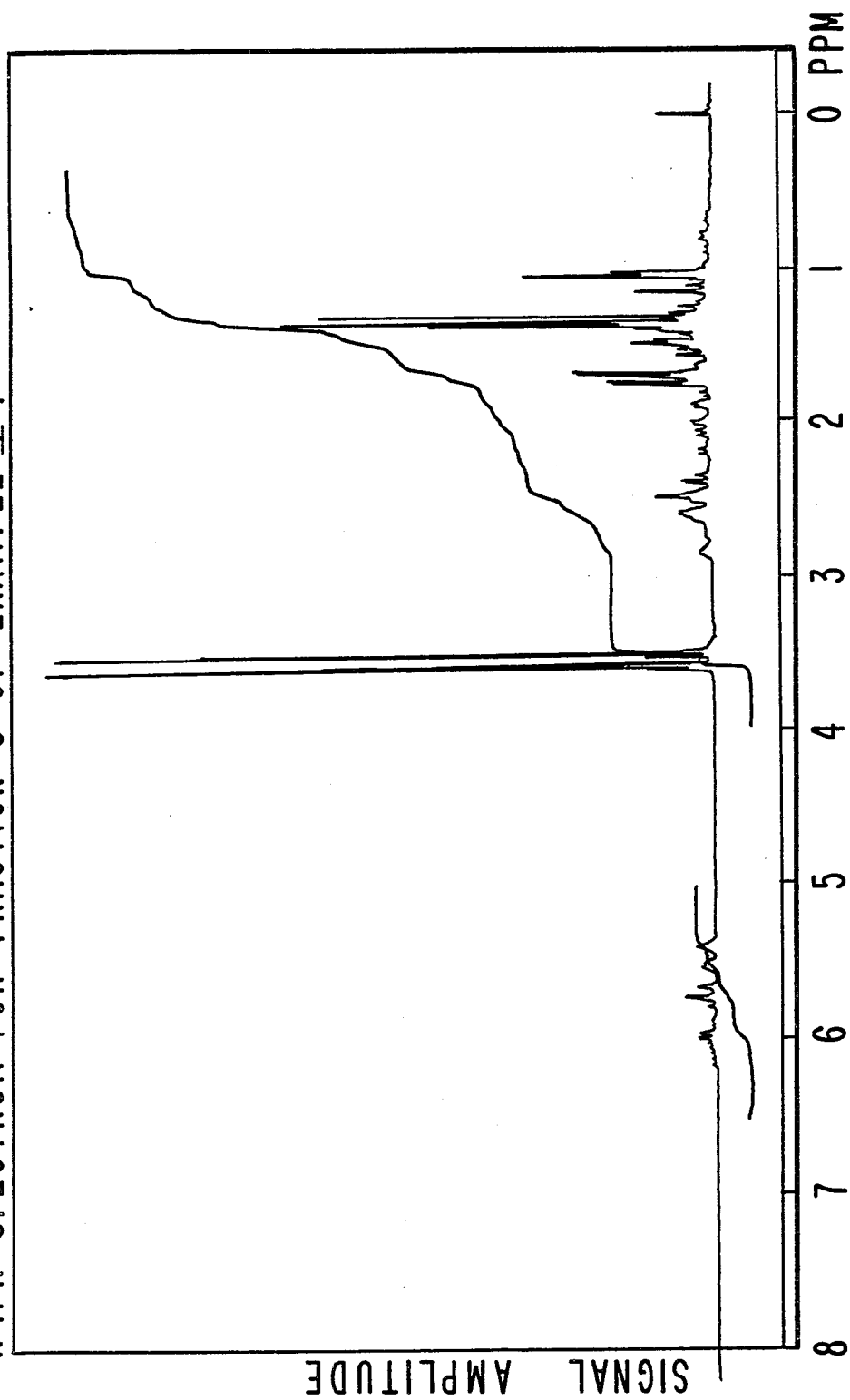
FIG. 1 is the NMR spectrum for the substance produced according to the reaction of Example I, distillation fraction 5 consisting essentially of the compounds having the structures.

FIG. 1 is the NMR spectrum for fraction 5 of the foregoing distillation containing the compounds having the structures:

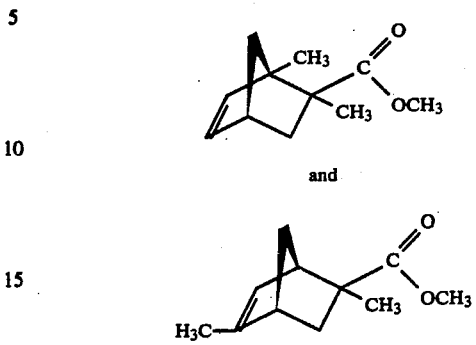

FIG. 2 is the infra-red spectrum for fraction 5 of the foregoing distillation containing the compounds having the structures:

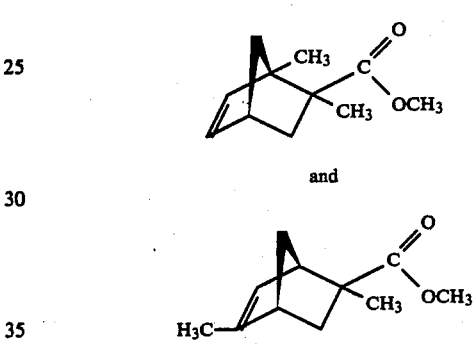

EXAMPLE II

Preparation of Methyl Ester of 2,5(and 6) Dimethyl-2-Norbornane Carboxylic Acid

Reaction:

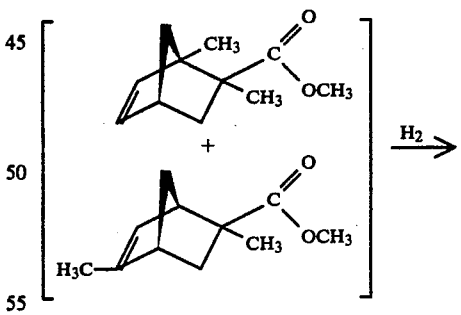

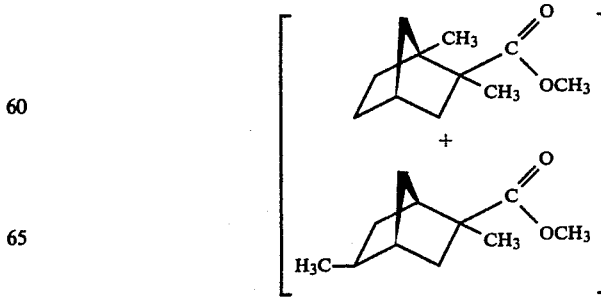

Into a pressure bottle is placed 226.0 grams (1.25 moles) of bulked fractions 2–12 of the distillation product of Example I containing the compounds having the structures:

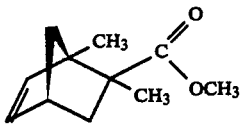

and

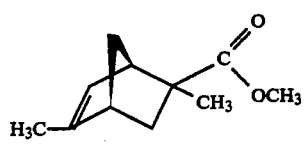

0.5 grams of 10% palladium on carbon; and 100 cc of anhydrous isopropyl alcohol. The pressure bottle is sealed under nitrogen. Hydrogenation is commenced and carried out over a period of 3.5 hours at which time the hydrogenation ceases. The hydrogenation is carried out at a pressure of 150 psig and at a temperature of 120° C.

At the end of the hydrogenation, the pressure bottle is opened and the reaction mass is filtered and the resulting filtrate is distilled to yield 199 grams (87% of theory). Distillation takes place on a 12" stone packed column yielding the following fractions:

| Fraction Number | Vapor Temp. (°C.) | Liquid Temp. (°C.) | Pressure mm/Hg. |
|---|---|---|---|
| 1 | 50/50 | 70/80 | 2.5/2.5 |
| 2 | 60 | 80 | 2.5 |
| 3 | 60 | 80 | 2.5 |
| 4 | 60 | 180 | 2.5 |

The resulting product is then redistilled on an 18" Goodloe column yielding the following fractions:

| Fraction Number | Vapor Temp. (°C.) | Liquid Temp. (°C.) | Pressure mm/Hg. |
|---|---|---|---|
| 1 | 55/60 | 65/70 | 2.9/2.5 |
| 2 | 60 | 70 | 2.0 |
| 3 | 65 | 80 | 2.0 |
| 4 | 54 | 71 | 1.0 |
| 5 | 54 | 105 | 1.0 |
| 6 | 50 | 220 | 1.0 |

FIG. 3 is the NMR spectrum for fraction 3 of the foregoing distillation containing the compounds having the structures:

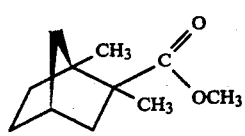

and

-continued

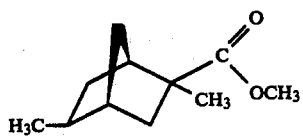

FIG. 4 is the infra-red spectrum for fraction 3 of the foregoing distillation containing the compounds having the structures:

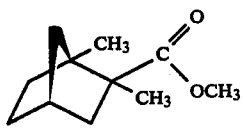

and

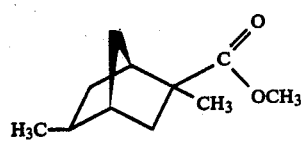

EXAMPLE III

The following spicy/woody/minty-type formulae are prepared:

| Ingredient | Parts by Weight III(A) | III(B) |
|---|---|---|
| Brazilian mint oil | 5.0 | 5.0 |
| Geranium bourbon | 15.0 | 15.0 |
| Lavendar oil barreme | 10.0 | 10.0 |
| Thyme oil white | 10.0 | 10.0 |
| Amyl cinnamic aldehyde | 10.0 | 10.0 |
| Sauge sclaree french | 5.0 | 5.0 |
| Sandalwood oil | 5.0 | 5.0 |
| Galbanum oil | 5.0 | 5.0 |
| Patchouli oil light | 5.0 | 5.0 |
| Cedarwood oil light | 15.0 | 15.0 |
| Product produced according to Example I, bulked fractions 2–12 containing and consisting of the compounds having the structures: | 5.0 | — |

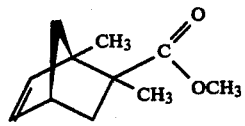

and

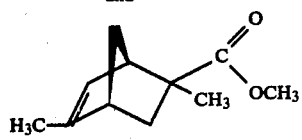

| | | |
|---|---|---|
| Product prepared according to Example II, containing bulked fractions 2–6 containing and consisting of the compounds having the structures: | — | 5.0 |

| Ingredient | Parts by Weight | |
|---|---|---|
| | III(A) | III(B) |

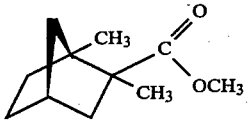

and

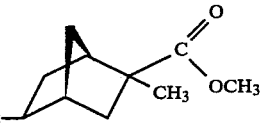

When the compositions of matter prepared according to Example I or II are incorporated into the formulae at 5.0%, both compositions of matter add a pleasant minty, woody, camphoraceous, aroma with patchouli-like undertones to the spicy/woody/minty-type perfume formulations.

EXAMPLE IV

A stable lotion is prepared with the following formulations:

| Ingredients | Parts by Weight |
|---|---|
| Poly(N,N—dimethyl-3,5-dimethyl-ene piperidinium chloride) (Merquat 100, Merck & Co., U.S.A., average molecular weight 50,000–100,000 viscosity in 40% aqueous solution, 100,000 cps.) | 1.0 |
| Cocoamidopropyl dimethyl glycine (betaine) | 5.7 |
| Myristyl dimethylamine oxide | 12.0 |
| Stearic monoethanolamide opacifier | 2.0 |
| Perfume material as indicated in Table II (below) giving rise to the aroma profiles as indicated in Table II below | 0.5 |
| Water, color, salts, U.V. absorber | q.s. to 100 |

Two or three bottle capfuls of the above lotion held under the tap releasing the water into the bathtub yields a copiously foamed bubble bath with no visible precipitation flocculation, or "bathtub ring" even using hard water. Bathing in this bath is found to have a cleansing and pleasing emollient effect on the skin as described above.

When, after immersion in this bath, the body is soaped, rinsed and dried, an even better, more long-lasting emollient, moisturizing effect on the skin is observed. The foam or bubbles are substantially unaffected by the soaping step, and no precipitate, flocculate or "bathtub ring", or any bothersome film or coating on the bathtub surface is found.

TABLE II

| Structure of Chemical | Organoleptic Properties in Fragrances |
|---|---|
| Mixture of compounds (as produced according to Example I) containing compounds having the structures: | A powerful, minty, camphoraceous, fruity aroma. |

TABLE II-continued

| Structure of Chemical | Organoleptic Properties in Fragrances |
|---|---|
| 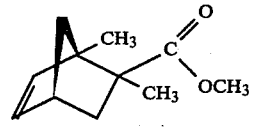 and 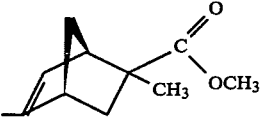 Mixture of compounds (produced according to Example II) containing the compounds having the structures: 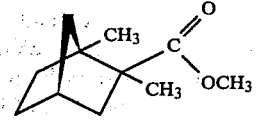 and 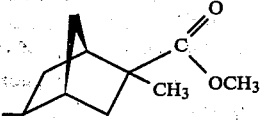 | A camphoraceous, sweaty, menthol-like aroma with patchouli-like undertones. |
| Perfume composition prepared according to Example III(A). | A spicy, woody, minty aroma profile with patchouli-like undertones. |
| Perfume composition prepared according to Example III(B). | A spicy, woody, minty aroma profile with patchouli-like undertones. |

EXAMPLE V

The following formulation is prepared with results in properties and use similar to those described in Example IV.

| Ingredients | Parts by Weight |
|---|---|
| "Merquat 100" | 1.0 |
| Cocoamidopropyl dimethyl glycine | 8.0 |
| Myristyl dimethyl amine oxide | 16.0 |
| Perfume ingredient as set forth in Table II of Example IV, supra, giving rise to the aroma profiles as set forth in Table II of Example IV, supra | 0.9 |
| Water | q.s. to 100 |

The composition is a clear liquid. Its viscosity may be increased by addition of a lauric or myristic diethanolamide or a soluble polyethylene glycol ester such as polyethylene glycol 6000. In addition, this composition may be rendered opaque by addition of stearic monoethanolamide stearate, polyethylene glycol 600 monostearate or a glyco amido stearate such as "Cerasynt 1P".

EXAMPLE VI

The following shampoo is prepared containing the following ingredients:

| Ingredients | Parts by Weight |
|---|---|
| Tridecyloxy polyethoxy ethanol of ten ethoxy groups | 17.3 |
| Polyoxyethylene (20) sorbitan monolaurate | 7.5 |
| Myristyl dimethylamine oxide (30% active) | 25.0 |
| $C_{10}-C_{20}$ fatty acyl monoethanolamide (cocomonoethanolamide) | 2.5 |
| Polyacrylamide of molecular weight of about 1,500,000 | 0.2 |
| Hydrogen peroxide (30% aqueous solution) | 0.5 |
| Perfume ingredient as indicated at Table II of Example IV, supra, giving rise to the aroma profiles as indicated in Table II of Example IV, supra | 1.0 |
| Deionized water (3 micromhos/cm conductivity) | 46.0 |

A shampoo of the above composition is made in the following matter. First, the tridecyloxy polyethoxy ethanol is added to a clean mixing tank, with the agitator on, and the amine oxide, polyoxyethylene sorbitan monolaurate and cocomonoethanolamine are added sequentially, with continued agitation. The mix is then heated to 68° C., until the cocomonoethanolamide is melted and/or dissolved. The hydrogen peroxide solution is then admixed with the mentioned nonionics and mixing is continued for about half an hour, in which the peroxide destroys any free amines or other harmful impurities that may be present. The mix is then cooled to 38° C.

In a separate mixer the polyacrylamide is gradually added to the formula weight of deionized water, with the mixer on. Addition is effected carefully and slowly (the polyacrylamide is sprinkled in) to avoid the production of "fish eyes" in the mix. After dissolving of the polyacrylamide the solution thereof is added to the first mixing tank with agitation and is blended with the nonionics, such mixings being at room temperature. Subsequently, the perfume as indicated in Table II of Example IV, supra, giving rise to the aroma profile as set forth in Table II of Example IV, supra, is admixed with the balance of the composition and mixing is continued for another half hour.

The product made is an excellent shampoo of satisfactory viscosity and aroma, foaming power, foam stability, low conductivity and good shampooing effects. The viscosity is about 1,000 centipoises at 20° C. and the conductivity, using the Hach Conductivity Meter, is 750 micromhos/cm. The foaming power is 250 ml and the foam stability is 22 seconds, by the test method previously described. In comparison, a commercial shampoo based on triethanolamine lauryl sulphate detergent has a conductivity of about 22,000 micromhos/cm, a viscosity of about 1,500 centipoises, a foaming power of about 380 ml and a foam stability of 60 seconds.

In panel evaluations of the experimental shampoo compared to a different commercial product, in actual shampooing, the experimental formula was adjudged significantly better in being less drying, producing a softer feel for the wet hair, leaving the wet hair easier to comb, being less prone to accumulate static charges (less flyaway) and having a foam of better appearance and feel. Additionally, the experimental product was judged better in almost all hair effect properties, with the control only being about equal to it in curl retention. In properties other than those mentioned the experimental product was better in rinsability, the control was better in foam build-up rate and the foams were about equal in volume and stability.

In the shampooing described herein and in subsequent Examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE VII

Fabric Freshener Composition

A fabric freshener composition is prepared as follows:

| Ingredients | Parts by Weight |
|---|---|
| Sodium bicarbonate | 3 |
| "Kyro" EOB (Trademark)* | 1 |
| Perfume ingredient as set forth in Table II of Example IV, supra, giving rise to an aroma as set forth in Table II of Example IV, supra | 1 |
| Water | 0.05 |

*A commercial nonionic surfactant comprising an average of eleven carbon atoms, ethoxylated to an average of 9 ethyleneoxy groups per molecule.

The composition of this Example is prepared by simply mixing the ingredients.

The above described composition is applied to a lightly soiled and wrinkled fabric as droplets (ca. 5.0 mm avg. size) using a trigger action sprayer having a nozzle which is adjustable to provide composition droplets in the desired range. The composition is applied at a rate of about 1 gram of composition to about 10 grams of fabric.

The fabric is then placed in an automatic dryer and dried, with tumbling action, at a temperature of 60° C.–80° C. for a period of 15 minutes. The fabric is rendered free of wrinkles and static, and has a fresh appearance and pleasant odor profile as set forth in Table II of Example IV, supra. Surprisingly, the sodium bicarbonate is not visible on the refreshed fabric.

In the foregoing procedure, substantially the same results were obtained when sodium carbonate is substituted for the sodium bicarbonate.

EXAMPLE VIII

Perfumed Liquid Detergent

Concentrated liquid detergents (lysine salts of n-dodecyl benzene sulfonic acid as more specifically described in U.S. Pat. No. 3,948,818, issued on Apr. 6, 1976) with aromas as indicated in Table II of Example IV, supra, are prepared containing 0.10%, 0.15%, 0.20%, 0.25%, 0.30%, 0.40%, 0.50% and 0.80% of the perfume ingredient as set forth in Table II of Example IV, supra. The detergents are prepared by adding and homogeneously mixing the appropriate quantity of perfume ingredient as set forth in Table II of Example IV, supra. The detergents all possess aromas as set forth in Table II of Example IV, supra with the intensity of each increasing with greater concentrations of the perfume ingredient as indicated in Table II of Example IV, supra.

EXAMPLE IX

Preparation Of A Cologne And Handkerchief Perfume

The perfume ingredient as set forth in Table II of Example IV, supra, is incorporated into colognes at concentrations of 2.0%, 2.5%, 3.0%, 3.5%, 4.0%, 5.0% and 6.0% in 75%, 80%, 85%, 90% and 95% aqueous ethanol solutions. Distinct and definite aromas as set forth in Table II of Example IV, supra, are imparted to the colognes. The perfume ingredients as indicated in Table II of Example IV, supra are also added to handkerchief perfumes at concentrations of 15%, 20%, 25%, 30% and 35% (in 75%, 80%, 85%, 90% and 95% aqueous ethanol) and aroma profiles as set forth in Table II of Example IV, supra are imparted to the handkerchief perfume.

EXAMPLE X

Blueberry Flavor Formulation

The following formulation is prepared:

| Ingredients | Parts by Weight |
| --- | --- |
| Heliotropin | 3.0 |
| Terpinenol-4 (10% in 95% aqueous food grade ethanol) | 0.2 |
| Benzaldehyde | 1.5 |
| Anisaldehyde | 0.2 |
| Phenyl acetaldehyde | 0.4 |
| Benzyl formate | 0.5 |
| Benzyl acetate | 2.0 |
| Cis-3-hexenyl benzoate (10% in 95% aqueous food grade ethanol) | 0.5 |
| Methyl hexanoate | 2.0 |
| Hexanal | 1.0 |
| Eucalyptol (1% in 95% aqueous food grade ethanol) | 0.5 |
| Eugenol | 0.2 |
| Acetaldehyde | 3.0 |
| Ethyl acetate | 21.0 |
| Ethyl butyrate | 26.0 |
| Propylene glycol | 38.0 |
| | 100.0 |

The above formulation is split into 5 portions. To the first four portions are added at the rate of 1%, the norbornane derivatives of Table I, supra. To the fifth portion, nothing is added. All five formulations with and without said norbornyl derivatives are combined with water at the rate of 100 ppm. The flavor of the first four portions each including a norbornyl derivative prepared according to the preceding examples as indicated in Table I, supra, have fruity, blueberry characteristics with several other nuances as indicated in Table I, supra, and are all closely similar to the flavor of wild blueberries. It is therefore preferred to use the formulations containing the norbornyl derivatives as listed in Table I, supra, to the basic blueberry formulation which does not contain any of said norbornyl derivatives.

EXAMPLE XI

Fruited Tapioca Cream

The contents of Ann Page Tapioca pudding mix (ingredients: sugar, corn starch, tapioca, sodium chloride, tapioca flavor and artificial color; net weight 138 grams) is emptied into a sauce pan. Three cups of milk are added together with one beaten egg yolk previously blended therewith. The resulting mix is cooked over medium heat stirring constantly while slowly adding at the rate of 0.2%, either one of the flavor materials of Example X (blueberry flavor) each of the materials containing one of the norbornyl derivatives of Table I, supra. The resulting mixture after heating, is then cooled to room temperature in the saucepan. One egg white is slowly added to the resulting mixture together with three tablespoons of sugar. The resulting mixture is then blended and chilled yielding pleasantly tasting blueberry tapioca cream desserts depending upon whether the materials of Example X are added.

EXAMPLE XII

Flavored Instant Pudding

A pudding mix (Royal Instant, net weight 3.5 ozs. produced by Standard Brands, Inc., New York, N.Y. 10022) is intimately admixed with 2 cups of cold fresh whole milk. To this mixture, at the rate of 0.3%, is added one of the blueberry flavors of Example X containing the norbornyl derivatives as listed in Table I, supra. The resulting mixture is blended in a Warning blender for a period of three minutes. The resulting mixture is then cooled at 15° C. for a period of five minutes. The resulting puddings have excellent natural blueberry flavors.

EXAMPLE XIII

A. Powder Flavor Composition 20 grams of the flavor composition of Example X (containing at least one of the norbornyl derivatives of Table I, supra) is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B. Sustained Release Flavor

The following mixture is prepared:

| Ingredients | Parts by Weight |
| --- | --- |
| Liquid blueberry flavor composition of Example X | 20 |
| Propylene glycol | 9 |
| Cab-O-Sil ® M-5 (brand of Silica produced by the Cabot Corp. of 125 High St. Boston, Mass. 02110; Physical properties: Surface area: 200 m²/gm Nominal particle size: 0.012 microns Density: 2.3 lbs./cu. ft. | 5 |

The Cab-O-Sil ® is dispersed in the liquid blueberry flavor composition (containing the norbornyl derivatives of Table I, supra) of Example X with vigorous stirring, thereby resulting in a viscous liquid. 71 parts by weight of the powder flavor composition of Part A, supra, is then blended into the said viscous liquid, with stirring, at 25° C. for a period of 30 minutes resulting in a dry, free-flowing sustained release flavor powder.

EXAMPLE XIV 10 parts by weight of 50 Bloom pigskin gelatin is added to 90 parts by weight of water at a temperature of 150° F. The mixture is agitated until the gelatin is completely dissolved and the solution is cooled to 120° F. 20 parts by weight of the liquid flavor composition of Example X (containing at least one of the norbornyl derivatives of Table I, supra) is added to the solution which is then homogenized to form an emulsion having particle size typically in the range of 2–5 microns. This material is kept at 120° F. under which conditions the gelatin will not jell.

Coacervation is induced by adding, slowly and uniformly, 40 parts by weight of a 20% aqueous solution of sodium sulfate. During coacervation, the gelatin molecules are deposited uniformly about each oil droplet as a nucleus.

Gelatin is effected by pouring the heated coacervate mixture into 1,000 parts by weight of 7% aqueous solution of sodium sulfate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XV 100 parts by weight of chicle are mixed with 4 parts by weight of the flavor prepared in accordance with Example XIII. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting blueberry flavor.

EXAMPLE XVI

Chewing Gum 100 parts by weight of chicle are mixed with 18 parts by weight of the flavor prepared in accordance with Example XIV. 300 parts of sucrose and 100 parts of corn syrup are then added. Mixing is effected in a ribbon blender with jacketed side walls of the type manufactured by the Baker Perkins Co.

The resulting chewing gum blend is then manufactured into strips 1 inch in width and 0.1 inches in thickness. The strips are cut into lengths of 3 inches each. On chewing, the chewing gum has a pleasant, long-lasting blueberry flavor.

EXAMPLE XVII

Toothpaste Formulation

The following separate groups of ingredients are prepared:

| Parts by Weight | Ingredients |
|---|---|
| Group "A" | |
| 30.200 | Glycerine |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalsium phosphate (dihydrate) |
| Group "C" | |
| 2.000 | Sodium N—lauroyl sarcosinate (foaming agent) |
| Group "D" | |
| 1.200 | Flavor material of Example XIII(B) |
| 100.000 total | |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste, when used in a normal toothbrushing procedure, yields a pleasant blueberry flavor, of constant strong intensity throughout said procedure (1–1.5 minutes).

EXAMPLE XVIII

Chewable Vitamin Tablets

The flavor material of Example XIII(B) (containing norbornyl derivatives of Table I, supra) is added to a chewable vitamin tablet formulation at the rate of 10 gm/Kg which chewable vitamin tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.00 |
| Vitamin $B_1$ (thiamine mononitrate 33⅓% (Hoffman La Roche) | 4.0 |
| Vitamin $B_2$ (roboflavin) as Rocoat ® roboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example XIII(B) containing norbornyl derivatives of Table I, supra | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 grams dry Vitamin A acetate and 0.6 grams Vitamin D are then added as beadlets. The entire blend is then compressed using concave punches at 0.5 grams each.

Chewing of the resultant tablets yields a pleasant long lasting, consistently strong blueberry flavor for a period of 12 minutes.

What is claimed is:

1. A process for augmenting or enhancing the aroma of a perfume composition or cologne comprising the step of adding to a perfume base or a cologne base an aroma augmenting or enhancing quantity of at least one norbornyl compound defined according to the structure:

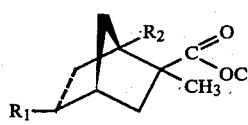

wherein the dashed line represents a carbon-carbon single bond or a carbon-carbon double bond and one of $R_1$ or $R_2$ is methyl and the other of $R_1$ or $R_2$ is hydrogen.

2. The process of claim 1 wherein the norbornyl derivative is a mixture of compounds having the structures:

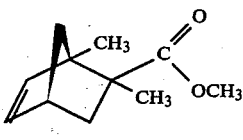

and

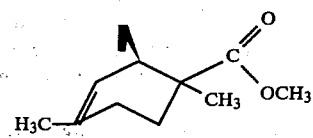

3. The process of claim 1 wherein the norbornyl derivative is a mixture of compounds having the structures:

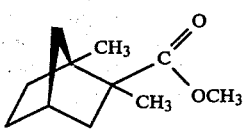

and

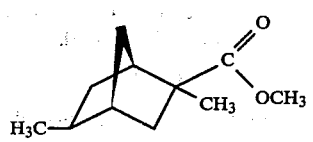

4. The process of claim 1 wherein the norbornyl derivative is added to a cologne and the cologne base comprises, in addition, ethanol and water.

* * * * *